United States Patent
Willson et al.

(10) Patent No.: US 12,092,641 B2
(45) Date of Patent: Sep. 17, 2024

(54) CHEMICAL DETECTION ASSAYS

(71) Applicants: Richard C. Willson, Houston, TX (US); Victoria M. Hlavinka, Houston, TX (US); Binh V. Vu, Houston, TX (US); Federico Augusto Ruiz-Ruiz, Houston, TX (US); Marco Antonio Rito Palomares, Houston, TX (US); Mary A. Crum, Houston, TX (US)

(72) Inventors: Richard C. Willson, Houston, TX (US); Victoria M. Hlavinka, Houston, TX (US); Binh V. Vu, Houston, TX (US); Federico Augusto Ruiz-Ruiz, Houston, TX (US); Marco Antonio Rito Palomares, Houston, TX (US); Mary A. Crum, Houston, TX (US)

(*) Notice: Subject to any disclaimer, the term of this patent is extended or adjusted under 35 U.S.C. 154(b) by 833 days.

(21) Appl. No.: 17/271,077

(22) PCT Filed: Aug. 22, 2019

(86) PCT No.: PCT/US2019/047708
§ 371 (c)(1),
(2) Date: Feb. 24, 2021

(87) PCT Pub. No.: WO2020/041591
PCT Pub. Date: Feb. 27, 2020

(65) Prior Publication Data
US 2022/0057406 A1    Feb. 24, 2022

Related U.S. Application Data

(60) Provisional application No. 62/722,409, filed on Aug. 24, 2018.

(51) Int. Cl.
| | | |
|---|---|---|
| *B01L 3/00* | (2006.01) |
| *B01F 23/00* | (2022.01) |
| *B01F 23/41* | (2022.01) |
| *B01F 101/23* | (2022.01) |
| *B23Q 17/24* | (2006.01) |
| *C12M 1/34* | (2006.01) |
| *C12Q 1/04* | (2006.01) |
| *C12Q 1/18* | (2006.01) |
| *C12Q 1/32* | (2006.01) |
| *C12Q 1/54* | (2006.01) |
| *C12Q 1/686* | (2018.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 21/76* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/66* | (2006.01) |
| *G01N 33/68* | (2006.01) |
| *G01N 33/72* | (2006.01) |

(52) U.S. Cl.
CPC ............. *G01N 33/66* (2013.01); *C12Q 1/32* (2013.01); *C12Q 1/54* (2013.01); *G01N 21/763* (2013.01); *G01N 33/723* (2013.01)

(58) Field of Classification Search
CPC .... G01N 33/66; G01N 21/763; G01N 33/723; C12Q 1/32; C12Q 1/54
See application file for complete search history.

(56) References Cited

U.S. PATENT DOCUMENTS 4,994,377 A * 2/1991 Nakamura ............... C12Q 1/26
                                                                     436/178
8,178,312 B2    5/2012 Buse et al.
(Continued)

FOREIGN PATENT DOCUMENTS

| AU | 2015201617 A1 * | 4/2015 | ............ A61B 5/15 |
| CN | 1180378 A * | 4/1998 | ......... C12N 9/2402 |
| CN | 108034694 A | 5/2018 | |
| JP | 2671104 B2 * | 10/1997 | ............. C12Q 1/26 |

OTHER PUBLICATIONS

Written Opinion dated Nov. 5, 2019 issued in International Application No. PCT/US2019/047708.
International Search Report dated Nov. 5, 2019 issued in International Application No. PCT/US2019/047708.
Woldman, Yakov Y. et al., Direct Chemiluminescent Detection of Nitric Oxide in Aqueous Solutions Using the Natural Nitric Oxide Target, Soluble Guanylyl Cyclase, Free Radic Biol Med., Nov. 15, 2009, vol. 47(10), pp. 1339-1345.

*Primary Examiner* — Jennifer Wecker
*Assistant Examiner* — Oyeleye Alexander Alabi
(74) *Attorney, Agent, or Firm* — Hunton Andrews Kurth LLP

(57) ABSTRACT

Disclosed are methods and kits for analyzing a sample comprising 1,5-anhydroglucitol and a possible first analyte via one or more chemiluminescent reactions. Certain embodiments include measuring a first light response resulting from a first chemiluminescent reaction and measuring a second light response resulting from a second chemiluminescent reaction. Certain embodiments also include comparing the first light response to the second light response to determine a ratio of 1,5-anhydroglucitol and the first analyte. Also provided are kits including reagents for practicing the claimed methods.

17 Claims, No Drawings

(56) References Cited

U.S. PATENT DOCUMENTS

| | | | |
|---|---|---|---|
| 2002/0068310 A1* | 6/2002 | Sasaki | C12Q 1/485 |
| | | | 435/14 |
| 2012/0094320 A1 | 4/2012 | Yoshioka et al. | |
| 2013/0316926 A1* | 11/2013 | Caffrey | C12Q 1/6886 |
| | | | 506/17 |
| 2017/0007215 A1 | 1/2017 | Podoly | |
| 2018/0031484 A1 | 2/2018 | Willson et al. | |

* cited by examiner

CHEMICAL DETECTION ASSAYS

CROSS REFERENCES

This application is the national phase of PCT/US2019/047708, filed on Aug. 22, 2019, which claims benefit of U.S. Provisional Application No. 62/722,409, filed on Aug. 24, 2018. Each of the aforementioned applications are incorporated in their entirety.

TECHNICAL FIELD

The present disclosure relates to the fields of chemistry, medicine, and diagnostics. More particularly, the present disclosure relates to methods for analyzing a body fluid sample. In particular embodiments, it relates to immuno- and luminescence-based assays for determining low levels of 1,5-anhydroglucitol (1,5-AHG, also written as 1,5-AG, AG, or AHG) in body fluid, particularly in saliva as a non-invasive screening, diagnostic, or monitoring method.

BACKGROUND

Damage to organs and tissues by type 2 diabetes (T2D) leads eventually to severe complications if diagnosis is not timely. 1,5-AHG is an unmetabolizable glucose analog which is present in human blood due predominantly to dietary ingestion. In physiology, the 1,5-AHG level is balanced by being reabsorbed and excreted through the kidney and urine, respectively. 1,5-AHG concentration in blood decreases during times of hyperglycemia since reabsorption is completely inhibited by glucose at fructose and mannose active transporter; Therefore, monitoring 1,5-AHG in saliva is useful in achieving glycemic control. A recent report has revealed a strong association of T2D with 1,5-AHG in saliva as a noninvasive marker, a benefit to patients who are averse to blood sampling. A principal aim of the present disclosure is efficient screening for undiagnosed diabetes by AHG measurement in saliva.

Pyranose oxidase (PROD) has been used for determining D-glucose and 1,5-AHG in blood in FDA-approved clinical analysis methods. PROD oxidizes the second position hydroxyl group of 1,5-AHG and generates hydrogen peroxide which can be detected using a variety of methods, including colorimetry, electrochemical and chemiluminescent assay. Therefore, 1,5-AHG is indirectly determined by measuring the generated hydrogen peroxide. However, saliva often contains D-glucose, which is also oxidized by PROD and produces hydrogen peroxide, thus, interferes with 1,5-AHG measurement. In this case, pretreatment of the sample is required to keep D-glucose from reaction with PROD. As such, a need currently exists for an improved technique for detecting analytes such as 1,5-AHG in body fluid samples.

SUMMARY

The present disclosure relates to methods for measuring an analyte, including, for example, 1,5-anhydroglucitol (1,5-AHG), in a body fluid sample. Certain embodiments include a method for analyzing a body fluid sample, where the method comprises obtaining and optionally pre-processing a sample comprising 1,5-anhydroglucitol; adding a first reagent to the sample, wherein the first reagent causes a chemiluminescent reaction with the sample; measuring a first light response resulting from the first chemiluminescent reaction; and optionally adding a second reagent to the sample. In particular embodiments, the second reagent is sequentially added to the sample after the first reagent is added to the sample; and the second reagent causes a second chemiluminescent reaction with the sample. In other embodiments, the sample can be split and different reagents added to the parts of the sample. Specific embodiments include measuring a second light response resulting from the second chemiluminescent reaction, and comparing the first light response to the second light response to determine a ratio of 1,5-anhydroglucitol and the first analyte.

In some embodiments, the present disclosure provides methods for analyzing a sample, the method comprising:
(a) obtaining a sample comprising of 1,5-anhydroglucitol and optionally a first species;
(b) adding a first reagent to the sample, wherein the first reagent causes a first chemiluminescent or bioluminescent reaction with 1,5-anhydroglucitol in the sample; and
(c) measuring a first light response resulting from the first chemiluminescent or bioluminescent reaction.

In some embodiments, the sample has been pretreated to remove the first species. In some embodiments, pretreating the sample comprises purifying the sample on an adsorbent or adding two or more enzymes to the sample.

In some embodiments, the methods further comprise:
(d) optionally adding a reagent or reagents to modify or remove species which could modify the signal obtained with 1,5-anhydroglucitol;
(e) observing the amount of light produced from the sample;
(f) observing the amount of light produced from the sample a second time after a first time period wherein the time period is sufficient that at least some preselected fraction of the 1,5-anhydroglucitol has been converted; and
(g) estimating the 1,5-anhydroglucitol from the light produced from the sample obtained in steps (e) and (f).

In other embodiments, the methods further comprise:
(d) optionally adding a reagent or reagents to modify or remove species which could modify the signal obtained with 1,5-anhydroglucitol;
(e) observing the amount of light produced from the sample;
(f) adding one or more additional reagents, wherein the one or more additional reagents are necessarily to cause the generation of 1,5-anhydroglucitol;
(g) observing the amount of light produced from the sample; and
(h) estimating the 1,5-anhydroglucitol from the light produced from the sample obtained in steps (e) and (g).

In other embodiments, the methods are further defined as:
(a) dividing the sample into at least two aliquots;
(b) adding to at least one aliquot a second reagent which modifies, captures or destroys 1,5-anhydroglucitol;
(c) adding to each aliquot the first reagent which causes a chemiluminescent or bioluminescent reaction with 1,5-anhydroglucitol in the sample;
(d) measuring the light response resulting from the chemiluminescent or bioluminescent reaction in each aliquot; and
(e) calculating a difference or ratio of the light signals obtained from each aliquot.

In other embodiments, the methods are further defined as:
(a) dividing the sample into at least two aliquots;
(b) adding to at least one aliquot a known amount of 1,5-anhydroglucitol;

(c) adding to each aliquot the first reagent which causes a chemiluminescent or bioluminescent reaction with 1,5-anhydroglucitol in the sample;
(d) measuring the light response resulting from the chemiluminescent or bioluminescent reaction in each aliquot; and
(e) calculating a difference or ratio of the light signals obtained from each aliquot.

In other embodiments, the methods are further defined as:
(a) dividing the sample into at least two aliquots;
(b) adding to at least one aliquot both a reagent which modifies, captures or destroys 1,5-anhydroglucitol and a known amount of 1,5-anhydroglucitol;
(c) adding to each aliquot the first reagent which causes a chemiluminescent or bioluminescent reaction with 1,5-anhydroglucitol in the sample;
(d) measuring the light response resulting from the chemiluminescent or bioluminescent reaction in each aliquot; and
(e) calculating a difference or ratio of the light signals obtained from each aliquot.

In some embodiments, the methods comprise:
(a) dividing the sample into at least three aliquots;
(b) adding to at least one aliquot a reagent which modifies, captures or destroys 1,5-anhydroglucitol;
(c) adding to at least one aliquot a reagent which modifies, captures or destroys a first species;
(d) adding to at least one aliquot a reagent which modifies, captures or destroys a first species and 1,5-anhydroglucitol
(e) adding to at least one aliquot a reagent which causes a chemiluminescent or bioluminescent reaction with first species in the sample;
(f) adding to at least two aliquot the first reagent which causes a chemiluminescent or bioluminescent reaction with 1,5-anhydroglucitol in the sample
(g) measuring the light response resulting from the chemiluminescent or bioluminescent reaction in each aliquot.
(h) calculating a difference or ratio of the light signals obtained from each of the aliquots.

In other embodiments, the methods further comprise:
(d) adding a second reagent to the sample, wherein:
 (i) the second reagent is added before or after the first reagent to the sample; and
 (ii) the second reagent causes a second chemiluminescent reaction with the first species in the sample; and
(e) measuring a second light response resulting from the second chemiluminescent reaction.

In some embodiments, the methods further comprise adding a third reagent or a second enzyme. In some embodiments, the methods further comprise:
(d') adding the third reagent to the sample, wherein:
 (i') the third reagent is sequentially added to the sample; and
 (ii') the third reagent causes a third chemiluminescent reaction with a second analyte in the sample; and
(e') measuring a third light response resulting from the third chemiluminescent reaction.

In some embodiments, the second reagent is added before the first reagent. In some embodiments, the third reagent is added before the first reagent. In some embodiments, the second reagent and the third reagent is added before the first reagent. In some embodiments, the methods further comprise (f) comparing the first light response to the second light response to determine a ratio of 1,5-anhydroglucitol and the first species.

In some embodiments, the sample comprises saliva. In other embodiments, the sample comprises urine. In other embodiments, the sample comprises blood. In other embodiments, the sample comprises interstitial fluid. In some embodiments, the methods comprise separating the sample into two or more aliquots.

In some embodiments, the first species is present and is selected from the group consisting of glucose, L-sorbose, D-xylose, D-galactose, glucono-δ-lactone, urea, creatinine, and creatine such as selected from the group consisting of glucose, L-sorbose, D-xylose, D-galactose, and glucono-δ-lactone. In some embodiments, the second species is selected from the group consisting of glucose, L-sorbose, D-xylose, D-galactose, glucono-δ-lactone, urea, creatinine, and creatine such as selected from the group consisting of urea, creatinine, and creatine. In some embodiments, the second reagent is selected from the group consisting of glucose oxidase, galactose oxidase, glucokinase, galactokinase, urease, sarcosine oxidase, AHG-6-phosphate dehydrogenase and creatinase such as selected from the group consisting of glucose oxidase, galactose oxidase, glucokinase, and galactokinase. In some embodiments, the third reagent is selected from the group consisting of glucose oxidase, galactose oxidase, glucokinase, galactokinase, urease, sarcosine oxidase, and creatinase such as selected from the group consisting of urease, sarcosine oxidase, and creatinase. In some embodiments, the first reagent and is selected from the group consisting of pyranose oxidase, sorbose dehydrogenase, hexokinase, and 1,5-anhydroglucitol specific dehydrogenase. In some embodiments, pyranose oxidase.

In some embodiments, the methods comprise adding an oxidant-removing or reductant-removing agent to the sample such as an oxidant-removing or reductant-removing agent selected from the group consisting of uricase, ascorbase, superoxide dismutase, and catalase.

In some embodiments, the first light response results from the reaction of a peroxidase, luminol, luciferase, a dioxetane, peroxyoxalate, or an acridine ester. In some embodiments, the second light response results from the reaction of a peroxidase, luminol, luciferase, a dioxetane, peroxyoxalate, or an acridine ester. In some embodiments, the first and second light responses result from the reaction of horseradish peroxidase or luminol. In some embodiments, measuring the first light response resulting from the first chemiluminescent reaction and the second light response resulting from the second chemiluminescent reaction comprises measuring photons with a light detector. In some embodiments, the light detector is selected from the group consisting of a charged coupled device (CCD), avalanche diode, multipixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellular phone camera, web camera, and smart watch camera.

In some embodiments, each of the reagents are added to the sample via a microfluidic device. In some embodiments, comparing the first light response to the second light response to determine a ratio of 1,5-anhydroglucitol and the second analyte comprises transmitting data to a computer processor. In some embodiments, the methods further comprise accessing a lookup table with the computer processor. In some embodiments, the lookup table comprises an indication of a physiological condition. In some embodiments, the physiological condition is related to an insulin or sugar or glycated hemoglobin level of a person from whom the sample was obtained. In some embodiments, the methods further comprise normalizing the ratio based on a measurement of a marker in the sample. In some embodiments, the marker is urea, creatinine, creatine, human serum albumin, or hemoglobin.

In still yet another aspect, the present disclosure provides kits comprising:
(a) saliva sampling instrument;
(b) pyranose oxidase, sorbose dehydrogenase, hexokinase, or 1,5-anhydroglucitol specific dehydrogenase; and
(c) a chemiluminescent reagent.

In particular embodiments, the sample comprises saliva, urine, blood, and/or interstitial fluid. In some embodiments, the first analyte is glucose, L-sorbose, D-xylose, D-galactose, glucono-δ-lactone, urea, creatinine, or creatine. In specific embodiments, the first reagent is glucose or galactose kinase, dehydrogenase, or oxidase, and or in some embodiments, the second reagent is pyranose oxidase, sorbose dehydrogenase, hexokinase, or 1,5-anhydroglucitol specific dehydrogenase. In specific embodiments, measuring the first light response resulting from the first chemiluminescent reaction and the second light response resulting from the second chemiluminescent reaction comprises measuring photons with a light detector.

In certain embodiments, the light detector is selected from the group consisting of a charged coupled device (CCD), avalanche diode, multi-pixel photon counter (MPPC), silicon photomultiplier (SiPMT), complementary metal-oxide semiconductor (CMOS) sensor, scientific CMOS (sCMOS) sensor, photomultiplier tube (PMT), photodiode, camera, cellular phone camera, web camera, or smartwatch camera. In particular embodiments, the first reagent and the second reagent are added to the sample via a microfluidic device. In some embodiments, comparing the first light response to the second light response to determine a ratio of 1,5-AHG and the first analyte comprises transmitting data to a computer processor. Specific embodiments further comprise accessing a lookup table with the computer processor. In certain embodiments, the lookup table comprises an indication or warning of a physiological condition or a potentially inaccurate test. In particular embodiments, the physiological condition is related to the insulin, glucose, or HbA1c level of a person from whom the sample was obtained. Some embodiments further comprise normalizing the ratio based on a measurement of a marker in the sample. In specific embodiments, the marker is urea, creatinine, creatine, human serum albumin, or hemoglobin. In certain embodiments, the sample comprises urine, blood or saliva.

In certain embodiments, the sample comprises tears saliva, urine, blood and/or interstitial fluid, or dried forms of these such as dried saliva spots or dried blood spots, or these along with preservatives, absorbents, or adsorbents. In some embodiments, saliva samples may be collected as whole saliva by draining, spitting, suction, or swab (absorbent) or as specific glandular secretions by cannulation, Lashley/Carlson-Crittenden cup, Wolff apparatus, or suction. Additionally, saliva production may be stimulated by common stimuli such as chewing gum, citric acid, or chewing on paraffin wax (e.g., Parafilm® M). In particular embodiments, the first analyte is glucose, urea, creatinine, or creatine. In some embodiments, the first reagent is glucose oxidase. In specific embodiments, the second reagent is pyranose oxidase. In certain embodiments, the first data comprises a first measure of photons relating to the first chemiluminescent reaction; and the second data comprises a second measure of photons relating to the second chemiluminescent reaction. In particular embodiments, the light detection device is selected from the group consisting of a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cell phone camera, web camera, or smartwatch camera. In some embodiments, the computer processor is configured to normalize the ratio based on a measurement of a marker in the sample. In specific embodiments, the marker is urea, creatinine, creatine, human serum albumin, or hemoglobin. In certain embodiments, the sample comprises urine, blood or saliva.

Exemplary embodiments of the present disclosure include chemiluminescence-based photon detectors for determining low-level 1,5-AHG in body fluid in a mobile format, including for example, as a smart phone accessory, for use in screening or monitoring diabetes. In one embodiment saliva AHG is measured along with or alternatively with blood AHG, glucose, or glycated protein such as hemoglobin, e.g., HbA1c, or glycated albumin. In one embodiment of the assay format, the inventors first oxidized 1,5-AHG in a sample solution with PROD to produce hydrogen peroxide, followed by adding 5-amino-2,3-dihydro-1,4-phthalaxinedione (luminol) and horseradish peroxidase (HRP). The emitted light from the luminol reaction was detected using photon sensors, including the avalanche photodiode (APD) arrays or photomultiplier tube (PMT).

Particular embodiments relate to luminescence-based assay and point-of-care (POC) photon detection for determining low-level analytes in body fluid, as a noninvasive screening method. In an assay format, an analyte of interest is treated with reagents in light-generating reactions to produce photons an output signal. The emitted photons are detected using a POC detector device that can be controlled and monitored via devices with computing and displaying capability, including, for example, mobile devices such as a smart phone.

Other embodiments relate to the use of an immunochemical, aptamer or another affinity measurement of AHG or a compound obtained from AHG by enzymatic or chemical transformation. These measurements may be made in a lateral- or vertical-flow format, or in a well plate or microfluidic device. In preferred embodiments, the assay format is competitive or anti-metatope, an antibody or other binding to AHG or a competitor is transduced to an optical signal such as light emission or fluorescence, or to an electrochemical signal such as electrochemiluminescence, current, or voltage.

Other embodiments relate to the electrochemical measurement of AHG or other biochemicals. In an embodiment, both glucose and galactose are enzymatically converted to non-interfering forms, for example by phosphorylation or oxidation, and then AHG is measured electrochemically. This electric chemical measurement may be made using an enzyme, by electrochemical impedance spectroscopy, by cyclic voltammetry, amperometry, or coulometry, optionally in the presence of a stabilizer or redox mediator. These measurements may involve the production of hydrogen peroxide, which is then measured electrochemically. AHG is preferably measured in saliva in these embodiments.

Saliva is preferably collected at least 30-90 minutes after eating or drinking. It may be diluted, filtered, precipitated, pH adjusted, heated, or treated with an adsorbent prior to the measurement. A known concentration of AHG may be spiked into an aliquot of the saliva, before or after sample preparation, as a separately-measured spike and recovery standard, used to calculate the AHG concentration in the original saliva sample.

Interfering glucose, ascorbic acid, uric acid, galactose, etc., may be enzymatically eliminated or converted by any of a variety of enzymes. In exemplary embodiments, glucose is eliminated or converted by oxidizing with glucose oxidase or phosphorylating glucose with hexokinase, with glucose oxidase and gluconolactonase or glucose dehydrogenase and gluconolactonase, or by reacting glucose into fructose-1,6-diphosphate with hexokinase, phosphohexose isomerase, and 6-phosphofructokinase or glucose isomerase, fructokinase, and 6-phosphofructokinase. Alternatively, glucose may be modified with glucokinase or hexokinase. In these modifications, glucose is converted to non-interfering compounds such as glucono-1,5-lactone, glucose-6-phosphate, gluconic acid, fructose-6-phosphate, or fructose-1,6-diphosphate. Similar enzymatic modifications of galactose and other biochemicals are well known, especially kinases and oxidoreductases.

In an embodiment, the analyte of interest is 1,5-anhydroglucitol, glucose, creatine, creatinine, urea, metabolites, a protein, a peptide, a hormone, a biomarker, a toxin, or a modified (e.g., phosphorylated or acetylated) protein.

In an embodiment, the saliva used for analysis is obtained using a dried saliva spot (DSS) sampling technique. In this method, saliva is first collected by passive drool in a vial and immediately spotted onto a filter paper and allowed to dry. After spotting, the dried saliva is extracted by an acetonitrile solution and vortexed for some time. Finally, the aqueous phase of the extraction is removed for analysis.

In accordance with an embodiment of this disclosure, a specimen is optionally pretreated for concentration of the analyte, removal of particulates, contaminants, interferences, or reaction inhibitors, reduction of viscosity, improvement of handling properties, or to modify the analyte for improved detection. Filtration, precipitation, and collection in porous matrices are favored pre-treatment methods.

In an additional embodiment, the methods to selectively remove or modify the interferences or contaminants include the uses of antibody capturing, aptamer capturing, enzymatic reactions, chemical modifications or chromatography techniques such as ion exchange, HIC, metal chelate, boronate, or affinity.

In an embodiment, the readout method by which the analyte is detected is the emission of light by chemiluminescence, bioluminescence, electrochemiluminescence, fluorescence, FRET, quenching or any method may be used for generating a light signal in the method of the present disclosure.

In an embodiment, the analyte is reacted to produce hydrogen peroxide through enzymatic coupled reaction. Hydrogen peroxide is detected by a chemiluminescent reaction with a chemiluminescent substrate to produce a light signal.

In an embodiment, the reagents used to generate light output are chemiluminescent substrates, such as luminol, isoluminol, luciferin, luciferin precursors, 1,2-dioxetanes, peroxyoxalate compounds, pyridine nucleotide detectors and dyes.

In an embodiment, the luminescent signal is generated by the reaction of a chemiluminescent substrate and hydrogen peroxide that is catalyzed by an enzyme, such as a peroxidase.

In an embodiment, the luminescent signal is generated by the reaction of a chemiluminescent substrate or precursor thereto, and reduced nicotinamide adenine dinucleotide (NADH) or reduced nicotinamide adenine dinucleotide phosphate (NADPH).

In another embodiment, the luminescent signal is generated by the reaction of a chemiluminescent substrate and hydrogen peroxide with metal nanoparticles, such as silver nanoparticles.

In an embodiment, the luminescent signal is obtained without enzyme by reacting luminol and hydrogen peroxide in the presence of a ferricyanide ion.

In an embodiment, the luminescent signal is obtained by reacting luminol and hydrogen peroxide in the presence of iron oxide nanoparticles.

In an embodiment, the luminescent signal is obtained by reacting luminol and hydrogen peroxide in the presence of a silver catalyst.

In an embodiment, the luminescent signal is obtained by reacting lucigenin with hydrogen peroxide in the presence of a metal ion.

In an embodiment, the luminescent signal is obtained by reacting an aryl oxalate such as bis(2,4,6-trichlorophenyl) oxalate with hydrogen peroxide in the presence of a fluorescent substance.

In an embodiment, the assay is done on a microfluidic device which comprises of multiple functional aspects: separation or removal of interferences, reaction to generate a signal, and optical signal readout areas. In an additional embodiment, the microfluidic device contains multiple separation/removal, reaction, and signal readout areas for multiplexing, where more than one analyte can be assessed. In an embodiment, the separation area in the microfluidic device contains adsorbent or absorbent to separate or remove interferences from analytes. In another embodiment, the separation area in the microfluidic device contains an enzyme to convert interferences to non-interferences.

In another embodiment, the interferences are enzymatically converted to hydrogen peroxide which reacts with a chemiluminescent substrate to generate a light signal. Interferences and hydrogen peroxide are consumed in the process and their signal, which is read by a light detector, can be used for calibration. Subsequence steps then convert analyte to a light signal and read out by a light detector.

In an embodiment, the luminescent signal output is collected by collection optics and subsequently detected by light detector such as but not limit to, charged coupled device (CCD), avalanche diode, (multi-pixel photon counter) MPPC or silicon photomultiplier (SiPMT), charged coupled device (CCD) sensor, complementary metal-oxide-semiconductor (CMOS) sensor, scientific CMOS (sCMOS) sensor, photomultiplier tubes (PMT). The light detector can function as a point-of-care device connected and controlled via wired or wireless connection by a personal computer, laptop, tablet, smartphone, smartwatch, or any similar devices with computing and displaying capabilities.

Certain terminology is used in the following description are for convenience only and is not limiting. The words "right," "left," "lower," and "upper" designate direction in the drawings to which reference is made. The words "inner", "outer" refer to directions toward and away from, respectively, the geometric center of the described feature or device. The words "distal" and "proximal" refer to directions taken in the context of the item described and, with regard to the instruments herein described, are typically based on the perspective of the surgeon using such instruments. The words "anterior," "posterior," "superior," "inferior," "medial," "lateral," and related words and/or phrases designate preferred positions and orientation in the human body to which reference is made. The terminology includes the above-listed words, derivatives thereof, and words of similar import.

In the following, the term "coupled" is defined as connected, although not necessarily directly, and not necessarily mechanically.

The use of the word "a" or "an", when used in conjunction with the term "comprising" in the claims and/or the specification, may mean "one," but it is also consistent with the meaning of "one or more" or "at least one." The terms "about," "approximately," or "substantially" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way but may also be configured in ways that are not listed.

Other objects, features, and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will be apparent to those skilled in the art from this detailed description

DETAILED DESCRIPTION

Early detection of type 2 diabetes (T2D) is important to reduce the complications of diabetes. T2D is a chronic metabolic disorder with markedly increasing presence in the world population in the past three decades. As discussed above, one of the major problems of T2D is that at early stages of disease development, practically no symptoms are observed, a reason to classify T2D as a silent disease. Healthy habits could be recommended for patients in order to improve life quality over the years. Nevertheless, considering that at early stages no signs can be easily detected, pre-diabetic patients tend to follow a non-healthy lifestyle which could increase the risk of heart failure, blindness, kidney failure, lower limb amputation and premature dead.

Molecular diagnostic techniques and point-of-care advances represent an important tool for the development of novel, fast and accurate assays for screening of chronic degenerative diseases, including T2D. For screening of type 2 diabetes, one can measure metabolites, such as 1,5-anhydroglucitol (1,5-AG), HbA1c and glucose in blood samples. Recent reports have established a strong association of type 2 diabetes with 1,5-AG in saliva. This makes 1,5-AG a promising non-invasive marker for point-of-care (POC) screening of type 2 diabetes because it does not require fasting or blood draws. Detecting 1,5-AG in saliva requires both highly sensitive assays and detectors.

The existing methods to detect 1,5-anhydroglucitol in blood use colorimetry as the readout signal. The 1,5-anhydroglucitol concentration in saliva and other body fluids is low, and there are a variety of interferents in saliva. Thus the current colorimetric assays would not be appropriate. The present disclosure concerns improved methods for assaying 1,5-anhydroglucitol and the devices to measure the assay signal. It is generalizable to other analytes, such as creatine and urea, and to other types of reporting methods. The emitted photons from the chemiluminescent reaction are detected using a photon detector device. A combination of chemistry optimization, interferent clearance, sensitive chemiluminescence-based assay and highly sensitive photon detector device allow the determination of low-level 1,5-anhydroglucitol. This disclosure describes assay methods potentially superior to our previously-disclosed chemiluminescent assays, as well as immunochemical and electrochemical detection of 1-deoxyglucose and other metabolites.

I. TYPE 2 DIABETES

Diabetes mellitus type 2 (also known as type 2 diabetes) is a long-term metabolic disorder that is characterized by high blood sugar, insulin resistance, and relative lack of insulin. Common symptoms include increased thirst, frequent urination, and unexplained weight loss. Symptoms may also include increased hunger, feeling tired, and sores that do not heal. Often symptoms come on slowly. Long-term complications from high blood sugar include heart disease, strokes, diabetic retinopathy which can result in blindness, kidney failure, and poor blood flow in the limbs which may lead to amputations. The sudden onset of hyperosmolar hyperglycemic state may occur; however, ketoacidosis is uncommon.

Type 2 diabetes primarily occurs as a result of obesity and lack of exercise. Some people are more genetically at risk than others. Type 2 diabetes makes up about 90% of cases of diabetes, with the other 10% due primarily to diabetes mellitus type 1 and gestational diabetes. In diabetes mellitus type 1 there is a lower total level of insulin to control blood glucose, due to an autoimmune induced loss of insulin-producing beta cells in the pancreas. Diagnosis of diabetes is by blood tests such as fasting plasma glucose, oral glucose tolerance test, or glycated hemoglobin (A1C).

Type 2 diabetes is partly preventable by staying a normal weight, exercising regularly, and eating properly. Treatment involves exercise and dietary changes. If blood sugar levels are not adequately lowered, the medication metformin is typically recommended. Many people may eventually also require insulin injections. In those on insulin, routinely checking blood sugar levels is advised; however, this may not be needed in those taking pills. Bariatric surgery often improves diabetes in those who are obese.

Rates of type 2 diabetes have increased markedly since 1960 in parallel with obesity. As of 2015, there were approximately 392 million people diagnosed with the disease compared to around 30 million in 1985. Typically, the age of onset is middle or older age, although rates of type 2 diabetes are increasing in young people. Type 2 diabetes is associated with a ten-year-shorter life expectancy. Diabetes was one of the first diseases described. The importance of insulin in the disease was determined in the 1920s.

The classic symptoms of diabetes are polyuria (frequent urination), polydipsia (increased thirst), polyphagia (increased hunger), and weight loss. Other symptoms that are commonly present at diagnosis include a history of blurred vision, itchiness, peripheral neuropathy, recurrent vaginal infections, and fatigue. Many people, however, have no symptoms during the first few years and are diagnosed during routine testing. A small number of people with type 2 diabetes mellitus can develop a hyperosmolar hyperglycemic state (a condition of very high blood sugar associated with a decreased level of consciousness and low blood pressure).

Type 2 diabetes is typically a chronic disease associated with a ten-year-shorter life expectancy. This is partly due to a number of complications with which it is associated, including two to four times the risk of cardiovascular disease, such as ischemic heart disease and stroke, a 20-fold increase in lower limb amputations, and increased rates of hospitalizations. In the developed world, and increasingly elsewhere, type 2 diabetes is the largest cause of nontraumatic blindness and kidney failure. It has also been associated with an increased risk of cognitive dysfunction and dementia through disease processes such as Alzheimer's disease and vascular dementia. Other complications include acanthosis *nigricans*, sexual dysfunction, and frequent infections.

Type 2 diabetes is due to insufficient insulin production from beta cells in the setting of insulin resistance. Insulin resistance, which is the inability of cells to respond adequately to normal levels of insulin, occurs primarily within the muscles, liver, and fat tissue. In the liver, insulin normally suppresses glucose release. However, in the setting of insulin resistance, the liver inappropriately releases glucose into the blood. The proportion of insulin resistance versus beta cell dysfunction differs among individuals, with some having primarily insulin resistance and only a minor defect in insulin secretion and others with slight insulin resistance and primarily a lack of insulin secretion.

Other potentially important mechanisms associated with type 2 diabetes and insulin resistance include increased breakdown of lipids within fat cells, resistance to and lack of incretin, high glucagon levels in the blood, increased retention of salt and water by the kidneys, and inappropriate regulation of metabolism by the central nervous system. However, not all people with insulin resistance develop diabetes, since impairment of insulin secretion by pancreatic beta cells is also required.

The World Health Organization definition of diabetes (both type 1 and type 2) is for a single raised glucose reading with symptoms, otherwise raised values on two occasions, of either:

fasting plasma glucose ≥7.0 mmol/l (126 mg/dl), or
a plasma glucose ≥11.1 mmol/l (200 mg/dl) following an oral glucose tolerance test A random blood sugar of greater than 11.1 mmol/l (200 mg/dl) in association with typical symptoms or glycated hemoglobin ($HbA_{1c}$) concentration of ≥48 mmol/mol (≥6.5 DCCT %) is another method of diagnosing diabetes. In 2009 an International Expert Committee that included representatives of the American Diabetes Association (ADA), the International Diabetes Federation (IDF), and the European Association for the Study of Diabetes (EASD) recommended that a threshold of ≥48 mmol/mol (≥6.5 DCCT %) should be used to diagnose diabetes. This recommendation was adopted by the American Diabetes Association in 2010. Positive tests should be repeated unless the person presents with typical symptoms and blood sugars >11.1 mmol/l (>200 mg/dl).

The threshold for diabetes diagnosis is based on the relationship between results of glucose tolerance tests, fasting glucose or $HbA_{1c}$ and complications such as retinal problems. A fasting or random blood sugar is preferred over the glucose tolerance test, as they are more convenient for people. Although fasting is not required, and concentration of the analyte remains stable in the body for a longer period of time than glucose, $HbA_{1c}$ testing is a more expensive procedure than a typical blood glucose measurement. It is estimated that 20% of diabetes cases in the United States are undiagnosed, meaning that one-fifth of diabetics are unaware that they have the disease.

Diabetes mellitus type 2 is characterized by high blood glucose in the context of insulin resistance and relative insulin deficiency. This is in contrast to diabetes mellitus type 1, in which there is an absolute insulin deficiency due to the destruction of islet cells in the pancreas and gestational diabetes mellitus that is a new onset of high blood sugars associated with pregnancy. Type 1 and type 2 diabetes can typically be distinguished based on the presenting circumstances. If the diagnosis is unclear, antibody testing may be useful to confirm type 1 diabetes, and C-peptide levels may be useful to confirm type 2 diabetes, with C-peptide levels normal or high in type 2 diabetes, but low in type 1 diabetes.

Management of type 2 diabetes focuses on lifestyle interventions, lowering other cardiovascular risk factors, and maintaining blood glucose levels in the normal range. Self-monitoring of blood glucose for people with newly diagnosed type 2 diabetes may be used in combination with education. However, the benefit of self monitoring in those not using multi-dose insulin is questionable. In those who do not want to measure blood levels, measuring urine levels may be done. Managing other cardiovascular risk factors, such as hypertension, high cholesterol, and microalbuminuria improves a person's life expectancy. Decreasing the systolic blood pressure to less than 140 mmHg is associated with a lower risk of death and better outcomes. Intensive blood pressure management (less than 130/80 mmHg) as opposed to standard blood pressure management (less than 140/85-100 mmHg) results in a slight decrease in stroke risk but no effect on overall risk of death.

Intensive blood sugar lowering ($HbA_{1c}$<6%), as opposed to standard blood sugar lowering ($HbA_{1c}$ of 7-7.9%), does not appear to change mortality. The goal of treatment is typically an $HbA_{1c}$ of 7 to 8% or a fasting glucose concentration of less than 7.2 mmol/L (130 mg/dl). However these goals may be changed after professional clinical consultation, taking into account the particular risks of hypoglycemia and life expectancy. Despite guidelines recommending that intensive blood sugar control be based on balancing immediate harms with long-term benefits, many people—for example, people with a life expectancy of fewer than nine years who will not benefit, are over-treated.

It is recommended that all people with type 2 diabetes receive routine eye examinations. There is weak evidence suggesting that treating gum disease by scaling and root planing may result in small, short-term improvement in blood sugar levels for people with diabetes. There is no evidence to suggest that the improvement in blood sugar levels is maintained for longer than 4 months. There is also not enough evidence to determine if medications to treat gum disease are effective at lowering blood sugar levels.

II. 1,5-ANHYDROGLUCITOL 1,5-Anhydroglucitol, also known as 1,5-AHG, is a naturally occurring monosaccharide found in nearly all foods.

Blood concentrations of 1,5-anhydroglucitol decrease during times of hyperglycemia above 180 mg/dL and return to normal levels after approximately 2 weeks in the absence of hyperglycemia. As a result, it can be used for people with either type-1 or type-2 diabetes mellitus to identify glycemic variability or a history of high blood glucose even if current glycemic measurements such as hemoglobin A1c ($HbA_{1c}$) and blood glucose monitoring have near normal values. Despite this possible use and its approval by the FDA, 1,5-AHG tests are rarely ordered. There is some data suggesting that 1,5-AG values are useful to fill the gap and offer complementary information to $HbA_{1c}$ and fructosamine tests.

The role of 1,5-AG was first inferred in 1981 when it was demonstrated decreased 1,5-AHG levels in diabetic patients. This observation was enhanced in 1983 when it was seen that plasma 1,5-AHG fell to undetectable levels in diabetic patients who did not receive insulin. Further studies showed that patients receiving medication to lower blood glucose had lasting improvement in 1,5-AHG levels. If medication stopped, 1,5-AHG decreased to pre-treatment levels. In 2003, 1,5-AG began to be looked at by researchers in the United States and was shown to be a valuable short-term glycemic monitor. In 2006, 1,5-AHG showed its most compelling clinical use when it was demonstrated that an assay (GlycoMark, developed by Nippon Kayaku, Inc.) for postprandial hyperglycemia was able to differentiate two patients who had similar, near goal, hemoglobin A1c values, yet very different glucose profiles as shown by continuous blood glucose monitoring—one of the patients having excessive glycemic variability. In 2014, 1,5-AHG in saliva was shown to mirror 1,5-AHG in blood, indicating that it could be used as a non-invasive marker of short-term glycemic control.

The current type of assay measures blood levels of 1,5-anhydroglucitol. 1,5-AHG is ingested from nearly all foods during the course of a regular diet. It is nearly 100% non-metabolized and remains in a relatively constant amount in the blood and tissues. 1,5-AHG is carried in the bloodstream and filtered by the glomerulus, where it enters the kidney. Once in the kidney, 1,5-AHG is re-absorbed back into the blood through the renal proximal tubule. A small amount, equal to the amount ingested, of 1,5-AHG is released via urine to maintain a constant amount in the blood and tissue. This process occurs in people who do not have their blood glucose values rising over 180 mg/dL.

When a diabetic person's blood glucose exceeds 180 mg/dL for any period of time, the kidney cannot re-absorb all glucose back into the blood. The rest is excreted in the urine (glucosuria). The additional glucose in the kidney blocks 1,5-AHG from being re-absorbed into the blood and 1,5-AG is excreted in the urine at a higher rate than normal. Blood levels of 1,5-AHG decrease immediately and continue to decrease until glucose values go below 180 mg/dL. Once hyperglycemia is corrected, 1,5-AHG begins to be reabsorbed from the kidney back into the blood at a steady rate. If a person's glucose levels remain below 180 mg/dL for approximately 4 weeks, 1,5-AHG will return to its normal levels.

It is this competitive inhibition of 1,5-AHG by glucose which allows assaying of 1,5-AHG to reflect any hyperglycemic episodes over 180 mg/dL accurately. A comprehensive evaluation of the assay has been described in the literature, as well as in U.S. Pat. No. 8,465,940, which is incorporated herein by reference. The assay can be run on almost any open chemistry analyzer, including those found in physician office laboratories. Two reactions take place during the measurement:

Reaction 1 is a pretreatment of the sample performed by adding glucokinase to convert glucose to glucose 6-phosphate in the presence of adenosine triphosphate, pyruvate kinase, and phosphoenol pyruvate. The purpose of this step is to alter glucose, which is found in the blood sample, so that it cannot react during reaction 2.

Reaction 2 uses pyranose oxidase to oxidize the second hydroxyl of 1,5-AG, generating hydrogen peroxide. The amount of hydrogen peroxide is detected by colorimetry using peroxidase, which is in direct relationship to the serum 1,5-AG concentration.

Results are presented in µg/mL. Lower values indicate worsening glucose control, with more frequent and prolonged glucose values over 180 mg/dL. 10 µg/mL of 1,5-AG correlates to an average post-meal glucose of 185 mg/dL and is the target value in people with diabetes. Values over 10 µg/mL indicate glucose on average is below 180 mg/dL. Those with values below 10 µg/mL could benefit from nutritional counseling and medications which target post-meal glucose spikes, such as pramlintide, exenatide, sitagliptin, saxagliptin, repaglinide or rapid-acting insulins.

| GlycoMark (µg/mL) | Approximate Mean Postmeal Maximum Glucose (mg/dL) |
|---|---|
| >12 | <180 |
| 10 | 185 |
| 8 | 190 |
| 6 | 200 |
| 4 | 225 |
| <2 | >200 |

III. METHODS OF DETECTING 1,5-AHG

In this embodiment, a sample containing 1,5-anhydroglucitol and possibly another analyte that would be detected. In particular embodiments, the other analyte may be glucose, galactose, urea, creatinine, and/or creatine.

In this embodiment, an initial step to pre-treat the specimen to concentrate the analyte, remove particulates, contaminants, interferences, or reaction inhibitors, reduce viscosity, improve handling properties, or to modify the analyte for improved detection may be employed. Filtration, precipitation, and collection in porous matrices are favored pre-treatment methods. Enzymatic depletion of interferences is also suitable and would involve depleting compounds similar to 1,5-anhydroglucitol that could be falsely detected as the analyte of interest.

In this embodiment, a first reagent may be added to detect another analyte in the sample, producing a first chemiluminescent reaction light response. Following this step, the first light response is measured.

In this embodiment, a first reagent is added to produce another chemical species from 1,5-anhydroglucitol that will be detected in the following step. In particular embodiments, this reagent may be pyranose oxidase, sorbose dehydrogenase, hexokinase, or 1,5-anhydroglucitol dehydrogenase.

In this embodiment, a third reagent is sequentially added to the sample, where the third reagent causes the second chemiluminescent reaction with the species produced in the preceding step. Following the addition of the third reagent, the light response of the second chemiluminescent reaction is measured.

In particular embodiments, measuring the light response resulting from the first chemiluminescent reaction and the second light response resulting from the second chemiluminescent reaction comprises measuring photons with a light detector. In specific embodiments, the light detector may be a charged coupled device (CCD), avalanche diode, multipixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellular phone camera, web camera, or smartwatch camera.

In addition, this embodiment may have a step to compare the first light response to the second light response to determine a ratio of 1,5-anhydroglucitol and another analyte. In certain embodiments, comparing the first light response to the second light response to determine a ratio of 1,5-anhydroglucitol and the first analyte comprises transmitting data to a computer processor. In some embodiments, the lookup table may comprise an indication of a physiological condition, including, for example, a physiological condition that is related to an insulin level of a person from whom the sample was obtained.

It is understood that other embodiments of the present disclosure may include additional or fewer steps than those described above. Certain embodiments may comprise kits configured to perform methods such as those described herein.

The specimen to be used in the present disclosure may be body fluid to assay 1,5-AHG contained therein. An enzymatic chemiluminescent reaction will be carried out in order to emit light for detection with the apparatus disclosed in the present disclosure. One aspect of the present disclosure comprises removing all sugars such as glucose from such specimen that can react with the aforementioned chemiluminescent reaction, to give appropriate samples.

This can be carried out, for example, by using glucose phosphorylation or column depletion, according to the methods disclosed in Nowatzke W, et al. (2004), *Clinica Chimica Acta.* 350: 201-209 and Yabuuchi M, et al. (1989), *Clin. Chem.* 35/10, 2039-2043, respectively. Namely, glucokinase or any other glucose phosphorylation enzyme is added to the saliva sample, and the obtained mixture is incubated at the appropriate temperature and time, preferably at ambient temperature (20-40° C.), and from 5-10 minutes. This can be carried out alone or coupled to a depletion column method where the treated or untreated sample is passed through a column packed with a strong anion exchange resin to remove glucose, from sample.

Afterward, an electron acceptor, such pyranose oxidase is employed to generate hydrogen peroxide, which is employed as a substrate for any number of available methods that give a chemiluminescent response in the presence of any other substrates. The most commonly employed method employs the catalytic enzyme horseradish peroxidase (HRP) and luminol to show chemiluminescence.

Measurements may be made on multiple samples from the same person, or on multiple aliquots of a sample, and/or in multiple steps. Background, assay inhibition or response factor, spike recovery, or nonspecific signal may be observed or estimated from measurements on separate samples or sample aliquots, or by repeated measurements on the same sample, with or without addition of reagents. Measurements may be multiplexed, for example by time, color, voltage, or position. In one embodiment, background is measured after an analyte such as AHG has been significantly reduced by chemical or enzymatic conversion. In another embodiment, background is measured before an analyte reporting reagent such as an enzyme is contacted with a sample.

Aliquots of a sample may be treated separately, and the results combined. In one such example, one aliquot of a sample is depleted of analyte to allow estimation of background signal. In another example, one aliquot of a sample is spiked with a known quantity of analyte such as AHG to provide a reference for determination of analyte concentration in another aliquot of the same or a related sample. In another example, the concentration of analyte in a sample or aliquot is reduced, and a known concentration of analyte is added before the measurement. Compounds related to the analyte, interferents or inhibitors can be used in these methods.

Background, spike-recovery and reference measurements of these types may be combined to provide an estimate of AHG or other analyte concentration in a variety of known ways. These methods include dividing one value by another, subtracting one value from another, applying a multiplicative or scaling factor derived from one measurement to another, and/or establishing a curve fit, calibration curve, equation, or lookup table to be used in analysis of multiple measurements to estimate concentration.

IV. KITS

In certain embodiments, the elements described above are included in a one or more reaction kits compatible with the method and apparati of the present disclosure and can be presented in an easy-to-use manner. For example, reagents in the form of powders or films, optionally included in or packaged with an excipient, in either dry or liquid form. Furthermore, the kit may provide a standard reference in order to calibrate the apparatus, as well as instructions for treating samples, performing the reactions, and/or measuring the results.

The kits will thus comprise, in suitable container means, one or more reactants and/or detection reagent, optionally along with buffers, controls, and receptacles for mixing and reacting the same. The components of the kits may be packaged either in aqueous media or in lyophilized form. Receptacles may include at least one vial, test tube, flask, bottle, syringe or other container means, into which the reagents may be placed, or suitably aliquoted. The kits of the present disclosure will also typically include a means for containing the reagents and receptacles and any other element in close confinement for commercial sale. Such containers may include injection or blow-molded plastic containers into which the desired vials are retained.

V. EMBODIMENTS

1. A method for analyzing a sample, the method comprising:
    (a) obtaining a sample comprising of 1,5-anhydroglucitol and optionally a first species;
    (b) adding a first reagent to the sample, wherein the first reagent causes a first chemiluminescent or bioluminescent reaction with 1,5-anhydroglucitol in the sample; and
    (c) measuring a first light response resulting from the first chemiluminescent or bioluminescent reaction.
2. The method of embodiment 1, wherein the sample has been pretreated to remove the first species.

3. The method of embodiment 2, wherein pretreating the sample comprises purifying the sample on an adsorbent or adding two or more enzymes to the sample.

4. The method of embodiment 1, further comprising:
   (d) optionally adding a reagent or reagents to modify or remove species which could modify the signal obtained with 1,5-anhydroglucitol;
   (e) observing the amount of light produced from the sample;
   (f) observing the amount of light produced from the sample a second time after a first time period wherein the time period is sufficient that at least some pre-selected fraction of the 1,5-anhydroglucitol has been converted; and
   (g) estimating the 1,5-anhydroglucitol from the light produced from the sample obtained in steps (e) and (f).

5. The method of embodiment 1, further comprising:
   (d) optionally adding a reagent or reagents to modify or remove species which could modify the signal obtained with 1,5-anhydroglucitol;
   (e) observing the amount of light produced from the sample;
   (f) adding one or more additional reagents, wherein the one or more additional reagents are necessarily to cause the generation of 1,5-anhydroglucitol;
   (g) observing the amount of light produced from the sample; and
   (h) estimating the 1,5-anhydroglucitol from the light produced from the sample obtained in steps (e) and (g).

6. The method of embodiment 1 further defined as:
   (a) dividing the sample into at least two aliquots;
   (b) adding to at least one aliquot a second reagent which modifies, captures or destroys 1,5-anhydroglucitol;
   (c) adding to each aliquot the first reagent which causes a chemiluminescent or bioluminescent reaction with 1,5-anhydroglucitol in the sample;
   (d) measuring the light response resulting from the chemiluminescent or bioluminescent reaction in each aliquot; and
   (e) calculating a difference or ratio of the light signals obtained from each aliquot.

7. The method of embodiment 1 further defined as:
   (a) dividing the sample into at least two aliquots;
   (b) adding to at least one aliquot a known amount of 1,5-anhydroglucitol;
   (c) adding to each aliquot the first reagent which causes a chemiluminescent or bioluminescent reaction with 1,5-anhydroglucitol in the sample;
   (d) measuring the light response resulting from the chemiluminescent or bioluminescent reaction in each aliquot; and
   (e) calculating a difference or ratio of the light signals obtained from each aliquot.

8. The method of embodiment 1 further defined as:
   (a) dividing the sample into at least two aliquots;
   (b) adding to at least one aliquot both a reagent which modifies, captures or destroys 1,5-anhydroglucitol and a known amount of 1,5-anhydroglucitol;
   (c) adding to each aliquot the first reagent which causes a chemiluminescent or bioluminescent reaction with 1,5-anhydroglucitol in the sample;
   (d) measuring the light response resulting from the chemiluminescent or bioluminescent reaction in each aliquot; and
   (e) calculating a difference or ratio of the light signals obtained from each aliquot.

9. The method for analyzing a sample, the method comprising:
   (a) dividing the sample into at least three aliquots;
   (b) adding to at least one aliquot a reagent which modifies, captures or destroys 1,5-anhydroglucitol;
   (c) adding to at least one aliquot a reagent which modifies, captures or destroys a first species;
   (d) adding to at least one aliquot a reagent which modifies, captures or destroys a first species and 1,5-anhydroglucitol
   (e) adding to at least one aliquot a reagent which causes a chemiluminescent or bioluminescent reaction with first species in the sample;
   (f) adding to at least two aliquot the first reagent which causes a chemiluminescent or bioluminescent reaction with 1,5-anhydroglucitol in the sample
   (g) measuring the light response resulting from the chemiluminescent or bioluminescent reaction in each aliquot.
   (h) calculating a difference or ratio of the light signals obtained from each of the aliquots.

10. The method of embodiment 1, further comprising:
    (d) adding a second reagent to the sample, wherein:
       (i) the second reagent is added before or after the first reagent to the sample; and
       (ii) the second reagent causes a second chemiluminescent reaction with the first species in the sample; and
    (e) measuring a second light response resulting from the second chemiluminescent reaction.

11. The method according to any one of embodiments 1-10, wherein the method further comprises adding a third reagent or a second enzyme.

12. The method of embodiment 11, wherein the method further comprises:
    (d') adding the third reagent to the sample, wherein:
       (i') the third reagent is sequentially added to the sample; and
       (ii') the third reagent causes a third chemiluminescent reaction with a second analyte in the sample; and
    (e') measuring a third light response resulting from the third chemiluminescent reaction.

13. The method according to any one of embodiments 1-12, wherein the second reagent is added before the first reagent.

14. The method according to any one of embodiments 11-13, wherein the third reagent is added before the first reagent.

15. The method according to any one of embodiments 11-14, wherein the second reagent and the third reagent is added before the first reagent.

16. The method of embodiment 10, further comprising (f) comparing the first light response to the second light response to determine a ratio of 1,5-anhydroglucitol and the first species.

17. The method of embodiment 1, wherein the sample comprises saliva.

18. The method of embodiment 1, wherein the sample comprises urine.

19. The method of embodiment 1, wherein the sample comprises blood.

20. The method of embodiment 1, wherein the sample comprises interstitial fluid.

21. The method of embodiment 1, wherein the method comprises separating the sample into two or more aliquots.

22. The method of embodiment 1, wherein the first species is present and is selected from the group consisting of glucose, L-sorbose, D-xylose, D-galactose, glucono-δ-lactone, urea, creatinine, and creatine.

23. The method of embodiment 22, wherein the first species is selected from the group consisting of glucose, L-sorbose, D-xylose, D-galactose, and glucono-δ-lactone.
24. The method according to any one of embodiments 1-23, wherein the second species is selected from the group consisting of glucose, L-sorbose, D-xylose, D-galactose, glucono-δ-lactone, urea, creatinine, and creatine.
25. The method of embodiment 24, wherein the second species is selected from the group consisting of urea, creatinine, and creatine.
26. The method of embodiment 1, wherein the second reagent is selected from the group consisting of glucose oxidase, galactose oxidase, glucokinase, galactokinase, urease, sarcosine oxidase, AHG-6-phosphate dehydrogenase and creatinase.
27. The method of embodiment 26, wherein the second reagent is selected from the group consisting of glucose oxidase, galactose oxidase, glucokinase, and galactokinase.
28. The method according to any one of embodiments 1-27, wherein the third reagent is selected from the group consisting of glucose oxidase, galactose oxidase, glucokinase, galactokinase, urease, sarcosine oxidase, and creatinase.
29. The method of embodiment 28, wherein the third reagent is selected from the group consisting of urease, sarcosine oxidase, and creatinase.
30. The method of embodiment 1, wherein the first reagent and is selected from the group consisting of pyranose oxidase, sorbose dehydrogenase, hexokinase, and 1,5-anhydroglucitol specific dehydrogenase.
31. The method of embodiment 30, wherein the first reagent is pyranose oxidase.
32. The method according to any one of embodiments 1-31, wherein the method comprises adding an oxidant-removing or reductant-removing agent to the sample.
33. The method of embodiment 32, wherein the oxidant-removing or reductant-removing agent is selected from the group consisting of uricase, ascorbase, superoxide dismutase, and catalase.
34. The method according to any one of embodiments 1-33, wherein the first light response results from the reaction of a peroxidase, luminol, luciferase, a dioxetane, peroxyoxalate, or an acridine ester.
35. The method according to any one of embodiments 1-34, wherein the second light response results from the reaction of a peroxidase, luminol, luciferase, a dioxetane, peroxyoxalate, or an acridine ester.
36. The method according to any one of embodiments 1-35, wherein the first and second light responses result from the reaction of horseradish peroxidase or luminol.
37. The method of embodiment 1, wherein measuring the first light response resulting from the first chemiluminescent reaction and the second light response resulting from the second chemiluminescent reaction comprises measuring photons with a light detector.
38. The method of embodiment 37, wherein the light detector is selected from the group consisting of a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellular phone camera, web camera, and smart watch camera.
39. The method of embodiment 10, wherein each of the reagents are added to the sample via a microfluidic device.
40. The method of embodiment 16, wherein comparing the first light response to the second light response to determine a ratio of 1,5-anhydroglucitol and the second analyte comprises transmitting data to a computer processor.
41. The method of embodiment 40, further comprising accessing a lookup table with the computer processor.
42. The method of embodiment 41, wherein the lookup table comprises an indication of a physiological condition.
43. The method of embodiment 42, wherein the physiological condition is related to an insulin or sugar or glycated hemoglobin level of a person from whom the sample was obtained.
44. The method of embodiment 16, further comprising normalizing the ratio based on a measurement of a marker in the sample.
45. The method of embodiment 44, wherein the marker is urea, creatinine, creatine, human serum albumin, or hemoglobin.
46. A kit comprising:
   (a) saliva sampling instrument,
   (b) pyranose oxidase, sorbose dehydrogenase, hexokinase, or 1,5-anhydroglucitol specific dehydrogenase, and
   (c) a chemiluminescent reagent.

VI. EXAMPLES

The following examples are included to illustrate various aspects of the disclosure further. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Detection of 1,5-AHG with Enzymatic Reaction Pretreatment

Early diagnosis of type 2 diabetes (T2D) is paramount important to reduce the complications of diabetes. For the glycemic monitoring in T2D, one can measure metabolic analytes, such as 1,5-anhydroglucitol (1,5-AHG), HbA1c and glucose in blood samples. A recent report has revealed a strong association of T2D with 1,5-AHG in saliva as a non-invasive marker, which may benefit patients who adverse to blood sampling. 1,5-AHG is unmetabolizable glucose analog which is present in human blood due predominantly to dietary ingestion. In physiology, the 1,5-AHG level is balanced by being reabsorbed and excreted through kidney and urine, respectively. The normal range of 1,5-AHG level in the human body is around 6.8-32.3 μg/ml. 1,5-AHG concentration in blood decreases during times of hyperglycemia since reabsorption is completely inhibited by glucose at fructose and mannose active transporter; Therefore, monitoring 1,5-AHG in saliva is useful in achieving glycemic control. Another application of the present technology is the use of saliva measurements of AHG for ongoing monitoring of the glycemic control of diabetics who already have been diagnosed. In one embodiment, the present salivary monitoring technology would be combined with occasional measurements by established methods such as hemoglobin A1c or fasting blood glucose.

To determine the concentration of 1,5-AHG, conventional methods such as liquid chromatography, gas-liquid chromatography, HPLC, or mass spectrometry can be used. An alternative method is to use an enzymatic reaction assay. Pyranose oxidase (PROD) has been used for determining D-glucose and 1,5-AHG in clinical analysis. PROD oxidizes the second position hydroxyl group of 1,5-AHG and generates hydrogen peroxide which can be detected using a variety of methods. Therefore, 1,5-AHG is indirectly determined by measuring the generated hydrogen peroxide). However, saliva sample contains D-glucose, which is also oxidized by PROD and produces hydrogen peroxide, thus, interferes with 1,5-AHG measurement. In this case, pretreatment of the sample is required to keep D-glucose from reaction with PROD.

In this example, 1,5-AHG in saliva is measured by its reaction with sorbose dehydrogenase from *Sinorhizobium* sp. 97507 and nicotinamide adenine dinucleotide (NAD) or nicotinamide adenine dinucleotide phosphate (NADP) to produce 1,5-anhydrofructose (1,5-AHF), NAD(P)H, and hydrogen cations. A subsequent reaction of NAD(P)H with a pyridine nucleotide detection chemiluminescent substrate produces light which can be detected using a high sensitivity light detector. However, other monosaccharides present in saliva, such as D-glucose and D-galactose, are also reactive with sorbose dehydrogenase. Therefore, these compounds are first depleted by glucose oxidase and galactose oxidase or glucokinase and galactokinase.

In another modification, 1,5-AHG in saliva is measured by one of the products of its reaction with pyranose oxidase, 1,5-AHF. NAD(P)H-dependent 1,5-AHF reductase is used in addition to NAD(P)H to form NAD(P) and 1,5-AHG from the 1,5-AHF produced by the preceding reaction. The depletion of the NAD(P)H by this reaction is then measured by the light intensity produced by a pyridine nucleotide detection chemiluminescent substrate. In this modification, the depletion of other monosaccharide compounds is not required as they are not reactive with 1,5-AHF reductase.

In another modification, 1,5-AHG in saliva is measured by one of the products of its reaction with pyranose oxidase, 1,5-AHF. NAD(P)H-dependent 1,5-anhydromannitol forming reductase is used in addition to NAD(P)H to form NAD(P) and 1,5-anhydromannitol from the 1,5-AHF produced by the preceding reaction. The depletion of the NAD(P)H by this reaction is then measured by the light intensity produced by a pyridine nucleotide detection chemiluminescent substrate. In this modification, the depletion of other monosaccharide compounds is not required as they are not reactive with 1,5-anhydromannitol forming reductase.

In another modification, 1,5-AHG in saliva is measured by its reaction with hexokinase and adenosine triphosphate (ATP) to form 1,5-AHG-6-phosphate. Following this reaction, 1,5-AHG-6-phosphate dehydrogenase and NAD(P) are used to produce 1,5-AHF-6-phosphate, NAD(P)H, and hydrogen cations. A subsequent reaction of NAD(P)H with a pyridine nucleotide detection chemiluminescent substrate produces light which can be detected using a high sensitivity light detector. Although hexokinase is reactive with all hexoses, the 1,5-AHG-6-phosphate enzyme is specific to AHG-6-phosphate and will not react with other phosphorylated hexoses present after the hexokinase reaction.

In another modification, 1,5-AHG in saliva is measured by its reaction with 1,5-AHG-specific dehydrogenase and NAD(P) to form 1,5-AHF, NAD(P)H, and hydrogen cations. A subsequent reaction of NAD(P)H with a pyridine nucleotide detection chemiluminescent substrate produces light which can be detected using a high sensitivity light detector.

Example 2: Detection of 1,5-AHG with Aqueous-Two Phase Extraction (ATPS) and Enzymatic Reaction Pretreatment In a modification to Example 1, a saliva sample containing 1,5-AHG is pretreated by both ATPS and enzymatic depletion of interfering compounds. Here, a saliva sample is introduced to an ATPS system composed of polyethylene glycol (PEG)-potassium phosphate and water. After the saliva is mixed with the phase components, the system is allowed to settle. After settlement, the bottom, salt-rich phase is extracted. Following the extraction, enzymes used to deplete D-glucose and D-galactose, such as glucose oxidase, galactose oxidase, glucokinase, galactokinase, glucose dehydrogenase, or galactose dehydrogenase, are added to the extracted bottom phase. Finally, the concentration of 1,5-AHG in the saliva sample is measured using the methods previously shown in Example 1.

Example 3: Detection of 1,5-AHG with a Chromatography Column

In an example, the sample is run through a chromatography column, such as ion exchange, HIC, metal chelate, boronate, or affinity, to remove glucose and other interferences. The eluent containing 1,5-anhydroglucitol is mixed with 10 µL of pyranose oxidase for 5 mins at room temperature. After the reaction of pyranose oxidase and 1,5-anhydroglucitol, 30 µL of luminol solution and 1 µg/mL peroxidase are added to the 1,5-AHG solution, followed by light intensity measurement using the point-of-care (POC) photon detector.

Example 4: Additional Sample Pretreatment to Remove Interferences

Depending on the sample sources, the presence of some monosaccharides can interfere with the 1,5-AHG detection assay. Some of the known interferences when using pyranose oxidase as 1,5-AHG detection enzyme include D-glucose, L-sorbose, D-xylose, D-galactose, and glucono-δ-lactone. The complexity of pretreatment varies with the type of body fluids. In a normal blood sample, D-glucose is the major interference, requiring pretreatment methods as described in Examples 1 and 2. For samples from other body fluids, a mixture of enzymes is used instead of just glucose oxidase. Such enzyme mix contains enzymes that can convert or modify the interferences to non-interfering molecules. An example of the composition of the enzyme mix includes glucose oxidase, L-sorbose oxidase, D-xylose oxidase, D-galactose oxidase, glucono-δ-lactone oxidase.

Another configuration of the enzyme mix consists of using glucokinase and galactokinase with ATP to form D-glucose-6-phosphate and D-galactose-2-phosphate from D-glucose and D-galactose, respectively, which are unreactive with pyranose oxidase. Similarly, glucose dehydrogenase and galactose dehydrogenase NAD(P) can also deplete D-glucose and D-galactose to form species unreactive with pyranose oxidase-D-glucono-1,5-lactone and D-galactono-1,5-lactone. Additionally, other configurations include a combination of glucokinase/ATP and galactose dehydrogenase/NAD(P) or glucose dehydrogenase/NAD(P) in conjunction with galactokinase/ATP.

Example 5: Detection of 1,5-AHG in Microfluidic Device

In this example, the sample is applied to a microfluidic device then inserted into a reader, in which the sample is split into two fractions by the Y-junction in a microfluidic channel. The fractions are pumped to two separated reaction chambers. In the first reaction chamber, a solution containing glucose oxidase is pumped in and mixed with the sample to produce hydrogen peroxide from the oxidation of glucose. In the second chamber, reaction buffer containing or 1,5-AHG dehydrogenase is pumped and mixed in to produce NAD(P)H. After a specific time which allows the reactions to go to completion, the contents of the first reaction chamber are mixed with a chemiluminescent substrate followed by a light intensity measurement through the optical window with a (POC) photon detector. The signal from the first chamber is interpreted as glucose concentration. The content of the second reaction chamber is mixed with a bioluminescent substrate such as Promega NAD(P)H-Glo™ and followed by light intensity measurement thru the optical window with a photon detector. The signal is interpreted as the concentration of 1,5-anhydroglucitol. Corrected 1,5-anhydroglucitol concentration in the sample is calculated from the two signals or by lookup table using the values of the signals.

In another example, the enzyme in the first reaction chamber is galactose oxidase. Hydrogen peroxide is produced from the sample by oxidation of galactose. The signal from the first chamber is interpreted as galactose concentration.

In another example, the enzyme mix in the first reaction chamber contains glucose oxidase and galactose oxidase. Hydrogen peroxide is produced from the sample by oxidation of glucose and galactose. The signal from the first chamber is interpreted as glucose and galactose concentration.

Example 6: Detection of 1,5-AHG in Lateral Flow Assay (LFA) Format

In another example, a sample containing 1,5-anhydroglucitol is mixed with horseradish peroxidase and chemiluminescent substrate. The sample and reagent mixture is then applied to a membrane strip using lateral flow assay (LFA) technology. The membrane strip is composed of nitrocellulose, a glass fiber membrane such as Fusion 5, cellulose membrane, or any material that has wicking capability. The strip contains at least three enzyme lines, with glucose oxidase galactose oxidase being the first line and second line. Additional enzymes can be immobilized on the lines between the second and last lines. Pyranose oxidase is immobilized on the last line that the sample will encounter as it travels along the strip. As the sample moves over the glucose oxidase line (first line), glucose is oxidized by glucose oxidase to hydrogen peroxide. Hydrogen peroxide reacts with a chemiluminescent substrate with horseradish peroxidase as the enzyme to produce a light signal at the first line. The glucose depleted sample then travels to the second line where pyranose oxidase converts 1,5-anhydroglucitol to hydrogen peroxide. Hydrogen peroxide reacts with a chemiluminescent substrate with horseradish peroxidase as the enzyme to produce a light signal at the second line. A High sensitivity light detector, such as a CCD camera, PMT, avalanche diode, S-CMOS camera, CMOS camera, or high sensitivity smartphone camera, can be used to perform light intensity measurement of the lines. Intensity measurement from the first line is interpreted as glucose concentration, and the intensity measurement from the second line is interpreted as 1,5-anhydroglucitol concentration.

In another modification, a sample containing 1,5-anhydroglucitol is mixed with a chemiluminescent substrate. The sample and substrate mixture is then applied to a membrane strip using lateral flow assay (LFA) technology. The membrane strip is composed of nitrocellulose, a glass fiber membrane such as Fusion 5, cellulose membrane, or any material that has wicking capability. The strip contains four enzyme lines: the first line is glucose oxidase, the second line is horseradish peroxidase, the third line is pyranose oxidase, and the fourth line as is horseradish peroxidase. The ordering is in the flow direction of the sample that will encounter as it travels along the strip. The widths of the first and second lines are separately determined by the enzymatic reaction times of each enzyme. As the sample move over the glucose oxidase line (first line), glucose is oxidized by glucose oxidase to hydrogen peroxide. Hydrogen peroxide reacts with a chemiluminescent substrate with horseradish peroxidase on the second line as the enzyme to produce a light signal at the second line. The glucose depleted sample then travels to the third line where pyranose oxidase converts 1,5-anhydroglucitol to hydrogen peroxide. Hydrogen peroxide reacts with a chemiluminescent substrate with horseradish peroxidase on the fourth line as the enzyme to produce a light signal at the fourth line. A High sensitivity light detector, such as a CCD camera, PMT, avalanche diode, S-CMOS camera, CMOS camera, or high sensitivity smartphone camera, can be used to perform light intensity measurement of the lines. Intensity measurement from the second line is interpreted as glucose concentration, and the intensity measurement from the fourth line is interpreted as 1,5-anhydroglucitol concentration.

In another modification, a sample containing 1,5-anhydroglucitol is mixed with a chemiluminescent substrate. The sample and substrate mixture is then applied to a membrane strip using lateral flow assay (LFA) technology. The membrane strip is composed of nitrocellulose, a glass fiber membrane such as Fusion 5, cellulose membrane, or any material that has wicking capability. The strip contains two enzyme lines, with a mixture of glucose oxidase and horseradish peroxidase as the first line and mixture of pyranose oxidase and horseradish peroxidase as the second line, in which sample will encounter as it travels along the strip. As the sample move over the glucose oxidase line (first line), glucose is oxidized by glucose oxidase to hydrogen peroxide. Hydrogen peroxide reacts with a chemiluminescent substrate with horseradish peroxidase as the enzyme to produce a light signal at the first line. The glucose depleted sample then travels to the second line where pyranose oxidase converts 1,5-anhydroglucitol to hydrogen peroxide. Hydrogen peroxide reacts with a chemiluminescent substrate with horseradish peroxidase as the enzyme to produce a light signal at the second line. A High sensitivity light detector, such as a CCD camera, PMT, avalanche diode, S-CMOS camera, CMOS camera, or high sensitivity smartphone camera, can be used to perform light intensity measurement of the lines. Intensity measurement from the first line is interpreted as glucose concentration, and the intensity measurement from the second line is interpreted as 1,5-anhydroglucitol concentration.

In another example, 1,5-anhydroglucitol can be detected and measured in an indirect competitive chemiluminescent-lateral flow assay. The membrane strip is composed of nitrocellulose, glass fiber membrane such as Fusion 5, cellulose membrane, or any material that has wicking capability. The strip contains two lines: test line and control line. The test is an area where anti-1,5-anhydroglucitol antibody is immobilized. The control line is an area where anti-HRP antibody is immobilized. Sample containing 1,5-anhydroglucitol is mixed with known amount of HRP-1,5-anhydroglucitol conjugate. The mixture is applied to the membrane strip and migrates along the strip by capillary action. When reaching the area of the strip where the anti-1,5-anhydroglucitol antibody is immobilized, the 1,5-anhydroglucitol in the sample competed with HRP-1,5-anhydroglucitol for binding a fixed and limited amount of immobilized anti-1, 5-anhydroglucitol antibody. Unbound reagents continued to migrate until they reached the area of the strip where excess HRP-1,5-anhydroglucitol conjugate was captured by immobilized anti-HRP antibody. In the detection step, a chemiluminescent substrate for HRP is added to the strip and the resulting chemiluminescent signal is imaged using the high sensitivity light detector, such as a CCD camera, PMT, avalanche diode, S-CMOS camera, CMOS camera, or high sensitivity smartphone camera.

Example 7: Calibration Curve for Determining Glucose with the Use of Glucose Oxidase Phosphate buffer (monobasic and dibasic sodium phosphate) pH 6.5 at 0.2 M, TRIS-HCl Buffer, pH 8.5 at 50 mM, 3-(N-Ethyl-3-methylanilino)-2-hydroxy-propanesulfonic acid sodium salt (TOOS) at 10 mg/mL, 4-Aminoantipyrine (4-APP) 14 mg/mL, Glucose Oxidase at 18.3 U/mL, and HRP at 0.57 mg/mL (194 U/mg). 40 µL of a given dilution of glucose standard with 50 µg/ml concentration are mixed with 60 µL of a reagent containing 1 mL of TOOS, 1 mL of 4-APP, 1 mL of HRP and 7 mL of TRIS-HCl and 60 µL and 80 µL of a reagent containing 50 mL of phosphate buffer pH 6.5 and 5 mg of Glucose Oxidase. After 5 minutes, the absorbance of the reaction, carried out in transparent microplates of 96 wells is read at a wavelength of 546 nm in an Epoch reader (BioTek).

Example 8: Calibration Curve for Determining 1,5-AHG with the Use of Pyranose Oxidase 160 µL of a final reaction containing 32.14 mM of TRIS-HCl, pH 9, 10.71 mM of $MgCl_2$, 2.14 mM of ATP, 6.25 U/mL of Glucokinase, 6.56 mM of TRIS-HCl pH 8.5, 6.35 mM of TOOS, 129.16 mM of 4-APP, 1.07 U/mL of HRP and 2.18 U/mL of pyranose oxidase, with the correspondent dilutions of 1,5-AHG at 50 mg/mL are taken and absorbance read at 546 nm. The calibration curve can be created from the results.

Example 9: Calibration Curve to Quantify 1,5-AHG in Saliva

Standards of 1,5-AHG diluted in cleared saliva (i.e., saliva that has been depleted of pyran compounds such as glucose, galactose, and 1,5-AHG) are used as a calibration to quantify 1,5-AHG in a saliva sample. Dilutions of 1,5-AHG in PBS buffer at 5, 3.75, 2.5, 1.25, and 0 µg/mL are prepared, and 10 µL of each dilution are pipetted into a single well of a white 96-well half-area microplate. To each well, 40 µL of cleared saliva is added, making the final concentrations of the calibration standards 1, 0.75, 0.5, 0.25, and 0 µg/mL of 1,5-AHG in cleared saliva. Additionally, 10 µL of PBS and 40 µL of sample saliva (i.e., saliva that has been depleted of all pyran compounds except 1,5-AHG) are added to three separate wells. To begin the oxidation of 1,5-AHG, specific quantities of pyranose oxidase are added to each well, and the microplate is then incubated at 37° C. After incubating for some time, chemiluminescence reagent is added to each well, and the kinetic luminescence is immediately measured.

Example 10: Calibration Curve to Quantify Glucose in Saliva

Glucose standards diluted in glucose-free saliva (i.e., saliva that has been depleted of all glucose that appears naturally in the sample) are used as a calibration to quantify glucose in a saliva sample. Dilutions of glucose in PBS buffer at 500, 375, 250, 125, and 0 µg/mL are prepared, and 10 µL of each dilution are pipetted into a single well of a white 96-well half-area microplate. To each well, 40 µL of glucose-free saliva is added, making the final concentrations of the calibration standards 100, 75, 50, 25, and 0 µg/mL of glucose. Additionally, 10 µL of PBS and 40 µL of plain, untreated saliva are added to three separate wells. To begin the oxidation of glucose, specific quantities of glucose oxidase are added to each well, and the microplate is then incubated at 37° C. After incubating for some time, chemiluminescence reagent is added to each well, and the kinetic luminescence is immediately measured.

Example 11: Assay of Glucose Depletion with Use of Pretreatment Column

A column is filled with 100 µL of SP Sepharose (cation exchanger, user for the equilibration of the effluent), followed by 400 µL of Q Sepharose (anion exchanger). The column is washed with 500 µL of water (3×). After this, 100 µL of a sample, namely glucose or 1,5-AHG, are passed through the column. 10 µL of the effluent are assayed.

Example 12: Light Kinetics Obtained with the Use of HRP and Luminol

The reagents employed for this experiment are: HRP solution (270 ng/ml), $H_2O_2$ solutions (12.3-98 mM) and luminol (0.424 mg/L). These reagents are mixed in the next proportion in a black microplate: 35 µL of HRP, 75 µL of luminol and 50 µL of $H_2O_2$. The microtiter plate is then placed in a luminometer and measurements are taken every minute for 20 minutes.

Example 13: Full Method of 1,5-AHG Measurements with HRP and Luminol

This reaction buffer is prepared as following: 0.4 mL of 56.13 mg/mL $MgCl_2$, 0.6 mL of 66.13 mg/mL ATP, 0.7 mL distilled water are added to 8.4 mL of 75 mM TRIS-HCl PH 9. 80 µL of this reaction buffer are added to 10 µL of 1,5 AHG and 25 µL of water. The reaction buffer with 1,5 AHG is mixed with 35 µL of HRP, 75 µL of luminol and 60 µL of pyranose oxidase, and the luminescent signal is read for 20 min.

Example 14: 1,5-AHG Measurement with Lumigen® HyPerBlu Chemiluminescent Substrate Dilutions of 1,5-AHG standard solution in PBS buffer are distributed into a white microtiter plate. Pyranose oxidase or sorbose dehydrogenase is then added to each well. After incubation at 37° C., Lumigen® (Southfield, MI) HyPerBlu chemiluminescent substrate is added to each well in a 1:1 volume ratio and the luminescent signal is read for 30 min.

Example 15: 1,5-AHG Measurement with Promega NAD(P)H-Glo™ Detection System

Dilutions of a 1,5-AHG standard solution in PBS buffer are distributed into a white microtiter plate. NAD(P)H- dependent 1,5-AHF reductase, NAD(P)H-dependent 1,5-anhydromannitol forming reductase, 1,5-AHG-6-phosphate dehydrogenase, or 1,5-AHG-specific dehydrogenase is then added to each well. After incubation at 37°C, Promega (Madison, WI) NAD(P)H-Glo™ substrate is added to each well in a 1:1 volume ratio and the luminescent signal is read for 30 min. The chemiluminescent substrate contains a proluciferin reductase substrate that is reduced in the presence of NAD(P)H to form luciferin. The luciferin is then quantified by recombinant luciferase also present in the NAD(P)H-Glo™.

Example 16: 1,5-AHG Measurement and Calibrated with Glucose or Galactose Using NAD(P)H and Hydrogen Peroxide Detection System In this example, saliva sample containing 1,5-anhydroglucitol is treated with an enzyme mix containing glucose dehydrogenase and galactose dehydrogenase to remove glucose and galactose. Glucose and galactose are converted into D-glucono-1,5-lactone and D-galactono-1,5-lactone, respectively, with the generation of NAD(P)H. After incubation at 37° C., a bioluminescent substrate that reacts with NAD(P)H such as Promega NAD(P)H-Glo™ is added to the sample. The chemiluminescent substrate contains a proluciferin reductase substrate that is reduced in the presence of NAD(P)H to form luciferin. The light signal from reaction generated by luciferin and recombinant luciferase is read as the sample's internal calibrator.

Subsequently, pyranose oxidase is mixed with the treated sample to catalyze the oxidation of 1,5-anhydroglucitol to hydrogen peroxide. After the reaction with pyranose oxidase, a chemiluminescent reagent that reacts with hydrogen peroxide such as HyperBlu is added, then immediately followed light intensity measurement. Intensity measurement is interpreted as 1,5-anhydroglucitol concentration.

In a modification, the internal calibrator is generated by treating the saliva sample containing 1,5-anhydroglucitol with enzyme mix containing glucose kinase and galactose dehydrogenase. Glucose is converted glucose-6-phosphate. Galactose is converted to D-galactono-1,5-lactone with the generation of NAD(P)H. After incubation at 37° C., a bioluminescent substrate that reacts with NAD(P)H such as Promega NAD(P)H-Glo™ is added to the sample. The light signal from the reaction is read as the concentration of galactose and is used as internal calibrator.

In another modification, the internal calibrator is generated by treating the saliva sample containing 1,5-anhydroglucitol with enzyme mix containing glucose dehydrogenase and galactose kinase. Glucose is converted D-glucono-1,5-lactone with the generation of NAD(P)H. Galactose is converted to galactose-1-phosphate. After incubation at 37° C., a bioluminescent substrate that reacts with NAD(P)H such as Promega NAD(P)H-Glo™ is added to the sample. The light signal from the reaction is read as the concentration of glucose and is used as an internal calibrator.

Analytes. In exemplary embodiments, an analyte of interest may include 1,5-anhydroglucitol, glucose, creatine, creatinine, urea, metabolites, a protein, a peptide, a hormone, a biomarker, a toxin, or a modified (e.g., phosphorylated or acetylated) protein.

Analytes sources. In exemplary embodiments, the specimen in which the analyte is to be detected may comprise a biopsy specimen, blood, serum, plasma, stool, saliva, sputum, CSF, lavage fluid, nasal wash, urine, cell lysate, drinking water, natural water, sea water, soil water, soil leachate, fresh tissue, frozen tissue, neutral formalin-treated tissue, formalin fixed paraffin embedded tissue block, or an ethanol-fixed paraffin-embedded tissue block.

Sample pretreatment. In exemplary embodiments, a specimen may be optionally pretreated to concentrate the analyte, remove particulates, contaminants, interferences, or reaction inhibitors, reduce viscosity, improve handling properties, or to modify the analyte for improved detection. The methods to selectively remove or modify the interferences or contaminants include the uses of antibody capturing, aptamer capturing, enzymatic reactions, chemical modifications or chromatography techniques such as ion exchange, HIC, metal chelate, boronate, or affinity.

Reagents. In exemplary embodiments, the readout method by which the analyte is detected may be the emission of light by chemiluminescence, bioluminescence, or any method may be used for generating the light signal in the method of the present disclosure. Reagents to generate light output are chemiluminescent substrates, such as luminol, isoluminol, 1,2-dioxetanes, peroxyoxalate compounds and dyes, or bioluminescent substrates, such as luciferin. The signal generation reaction can be generated with or without enzyme. Among the available methods, oxidization of various chemiluminescent substrates with hydrogen peroxide catalyzed by peroxidase is the most common. There are other known methods for detecting hydrogen peroxide through chemiluminescence without using peroxidase, for example, the luminescence can be obtained with luminol and hydrogen peroxide in the presence of laccase. Luminescence can also be obtained without enzyme by reacting luminol and hydrogen peroxide in the presence of a ferricyanide ion, by reacting lucigenin with hydrogen peroxide in the presence of a metal ion, by reacting an aryl oxalate such as bis(2,4,6-trichlorophenyl) oxalate with hydrogen peroxide in the presence of a fluorescent substance, and by reacting luminol and hydrogen peroxide in the present of silver nanoparticles or iron oxide nanoparticles, or silver catalyst.

Assay apparatus. In exemplary embodiments, the assay may be done on a microfluidic device which comprises multiple functional aspects: separation or removal of interferences, reaction to generate a signal, and optical signal readout areas. In additional embodiments, the microfluidic device may contain multiple separation/removal, reaction, and signal readout areas for multiplexing, where more than one analyte can be assessed. The separation area in the microfluidic device contains adsorbent or absorbent to separate or remove interferences from analytes. In another embodiment, the separation area in microfluidic device contains an enzyme to convert interferences to non-interferences. The apparatus can be made by a 3D printer, injection mold, blow molding, extrusion molding, vacuum forming, compression molding or any other manufacturing techniques.

Detector devices. In exemplary embodiments, the luminescent signal output may be detected by a light detector such as, but not limited to, a charged coupled device (CCD), avalanche diode, (multi-pixel photon counter) MPPC or silicon photomultiplier (SiPMT), complementary metal-oxide semiconductor (CMOS) sensor, scientific CMOS (sCMOS) sensor, photomultiplier tubes (PMT), photodiode, camera, cell phone camera, web camera, smartwatch camera, or any light detector. The light detector can function as a point-of-care device connected and controlled via wired or wireless connection by a personal computer, laptop, tablet, smartphone, smart watch, or any similar devices with computing and displaying capabilities. The wireless connection includes, but is not limited to, Bluetooth, Wi-Fi, and near field communication (NFC).

The assay can be done in plate format wherein the signals are read by a plate reader equipped with photomultiplier tubes (PMT), an avalanche diode, multi-pixel photon counter (MPPC) or silicon photomultiplier (SiPMT), charged coupled device (CCD) sensor, complementary metal-oxide-semiconductor (CMOS) sensor, or scientific CMOS (sCMOS) sensor.

Example 17: Clearing of Inhibitors for Chemiluminescent Assays

Antioxidants are essential to the body's defense system. They neutralize free radicals, such as reactive oxygen species (ROS) that damage cells. The primary antioxidants in saliva include uric acid, ascorbic acid, albumin, glutathione and antioxidant enzymes. Their antioxidative activity can also interfere with a chemiluminescent reaction, which is an oxidation process. The presence of antioxidants in a chemiluminescent reaction can diminish or delay light signal output. In fact, the time delay of the light signal is sometimes used to quantify the concentration of antioxidants in the samples. The removal of these antioxidants is necessary for some chemiluminescent reactions, such as those using luminol-based reagents.

In an example, before the chemiluminescent reaction, 500 µl of saliva is treated with 0.05 U of uricase, 0.05 U of ascorbase, and enzymes and incubated for 10 min at 37° C. to remove small antioxidants that inhibit the chemiluminescent reaction. Catalase is added to remove hydrogen peroxide produced from the oxidation of these antioxidants. The sample is then filtered with a 3 kD molecular weight cut-off (MWCO) filter to remove the bigger antioxidant molecules such as superoxide dismutases (SODs), as well as catalase, etc. Similarly, these molecules may be removed by ion exchange or hydrophobic or metal-affinity chromatography or by heating the sample to a temperature known to denature the enzymes. Catalase-specific inhibitors, such as 3-amino-1,2,4-triazole, may also be used to impede the reduction of hydrogen peroxide during the chemiluminescent reaction. Once cleared of antioxidants, the metabolites in the sample can be assayed with chemiluminescent reaction read out.

Specifically, the inventors can measure glucose, galactose, and 1,5-anhydroglucitol (AHG) in one antioxidant-cleared sample. Antioxidant-cleared sample containing 1,5-anhydroglucitol is mixed with 10 µL of an enzyme mix containing glucose oxidase, peroxidase, and a chemiluminescent substrate, then immediately followed by light intensity measurement using the photon detector. The light signal is interpreted as glucose concentration. After the first reaction is completed, galactose oxidase is added then immediately followed by a light intensity measurement using the high sensitivity light detector. The signal is interpreted as galactose concentration. Finally, pyranose oxidase is added, then immediately followed by light intensity measurement using the photon detector. The signal is interpreted as AHG concentration. The ratio of 1,5-anhydroglucitol to glucose or galactose can be used to correct for the variations in sample collection.

In a modification, after 10 minutes incubation at 37° C. with enzymes to remove antioxidants, the sample is heated at 95° C. for 10 minutes to inactivate all the enzymes and other macromolecule antioxidants such as superoxide dismutases (SODs), catalase, etc. Once clear of antioxidants, the metabolites in the sample can be assayed with chemiluminescent reaction read out.

In another modification, before the chemiluminescent reaction, 500 µl of saliva collected by Salivette or free drooling is treated with 0.05 U of uricase, 0.05 U of ascorbase, glucose oxidase, galactose oxidase, and other to remove small antioxidants that inhibit the chemiluminescent reaction and to remove interferents in the AHG reaction. Catalase is also added to remove hydrogen peroxide produced from the oxidation of these antioxidants. The sample is incubated at 37° C. for 1 to 90 minutes, typically, 10 minutes. The sample is then filtered or heated to remove or inactivate the bigger antioxidant molecules such as superoxide dismutases (SODs), catalase, etc. Once clear of antioxidants and interferents, the AHG in the sample can be assayed with chemiluminescent reaction read out. Antioxidant and interferents cleared sample containing 1,5-anhydroglucitol is mixed with 10 µL of an enzyme mix containing pyranose oxidase, peroxidase and a chemiluminescent substrate, then immediately followed by light intensity measurement using the photon detector. The light signal is interpreted as AHG concentration.

In another example, before the chemiluminescent reaction, 500 µl of saliva sample is filtered or heated to remove or inactivate the bigger antioxidant molecules such as superoxide dismutases (SODs), catalase-like enzymes, etc. Saliva is then treated with 0.05 U of uricase, 0.05 U of ascorbase, and other enzymes and incubated for 10 minutes at 37° C. to convert small antioxidants that inhibit the chemiluminescent reaction to hydrogen peroxide. The hydrogen peroxide produced from the oxidation of these antioxidants is quantified by chemiluminescent reaction with HRP and luminol substrate. The signal can be used to normalize other measurements for dilution by saliva production. Once cleared of antioxidants, the sample can be assayed with conventional chemiluminescent reaction read out.

In a modification, the treated sample is urine. It is known that urine contains a high level of uric acid. Removal of uric acid and other antioxidants is necessary for assays using luminol-based chemiluminescent substrate. In another modification, the sample treated with the enzyme mix is blood, which contains catalase and other antioxidants. In another modification, the peroxidase is derived from sweet potato, or in a preferred modification, from soybean.

Alternatives to luminol chemistry. The presence of antioxidants in bodily fluids makes sensitive luminol-based chemiluminescent assay unreliable without any pretreatment. The presence of antioxidants in the chemiluminescent reaction can diminish or delay light signal output. Among the chemiluminescent methods to detect hydrogen peroxide, peroxyoxalate chemistry and acridinium ester chemistry are impervious to antioxidant interference.

Peroxyoxalate chemistry detection method. An example of a substrate for peroxyoxalate chemistry is bis(2,4,6-trichlorophenyl) oxalate (TCPO) which is used in glowsticks. Other variations of TCPO molecule have been synthesized for solvent compatibility and also can be used.

A fluorescer such as perylene is added at a concentration of 50 mg/l. The fluorescer can be chosen to spectrally match to the spectral sensitivity of an electronic detector to be used. A small amount of base catalyst, trimethylamine (50 µl/l) is added to make the chemiluminescent substrate. This TCPO substrate can be used to detect metabolites or other compounds in samples such as saliva, urine, blood, food, beverages, or natural or process waters. For example, a sample containing 1,5-anhydroglucitol is mixed with 10 µL of an enzyme mix containing glucose oxidase and TCPO chemiluminescent substrate, then immediately followed by light intensity measurement using the point-of-care (POC) photon detector. The light signal is interpreted as glucose concentration. After the first reaction completed, galactose oxidase is added then immediately followed by light intensity measurement for galactose signal. Finally, pyranose oxidase is added then immediately followed by a light intensity measurement using the high sensitivity light detector. The signal is interpreted as 1,5-anhydroglucitol concentration. The ratio of 1,5-anhydroglucitol to glucose can be used to correct for the variations in sample collection method.

Sample Preparation and Pre-concentration. When the target molecule is a low molecular weight monosaccharide, it may be processed according to traditional carbohydrate-concentration techniques, including thermal treatments.

As a first modification, a collected saliva sample can be concentrated using freeze concentration, or by a freeze-drying procedure similar to that reported by Daughters et al. First, a fresh sample is centrifuged at 4° C. and 1600×g for 15 min. The supernatant is transferred to a fresh 2 mL tube and the pellet discarded. The fresh cleared supernatant is then frozen for a 24 hr period at −80° C. Considering that the solvent of the sample is mainly water, the concentration step resides in a lyophilization step to be performed overnight (from 12-16 h approximately considering the nature and volume of the sample). After freeze-drying, samples should be stored at −20° C. It has been determined that freeze-dried saliva samples under these conditions are stable for molecular studies up to 2 weeks. After these procedures, the samples could be subjected to AHG content analysis.

A second protocol for sample concentration could include evaporative concentration. After collection of a saliva sample, the sample could be centrifuged at 15,000×g and 30 min at 24° C. The supernatant would then be transferred to a fresh 2 mL tube and then subjected to concentration with a GeneVac EZ-2 plus at 30° C. for 2 hr. A reduction of 10-15-fold in volume is achieved. Finally, concentrated samples are subjected to AHG content analysis. An alternative instrument that could be used in this approach is the Savant DNA 120 SpeedVac Concentrator (Thermo electron corporation).

In a third modification, a sample of saliva or urine, etc., is cleared of solids by centrifugation, then treated by addition of an equal volume of cool acetone or chloroform and held at 4° C. overnight (12-16 h). Then, a centrifugation step at 15,000×g for 30 min at 4° C. is performed, the supernatant then removed and treated with a Savant DNA 120 SpeedVac Concentrator. The final sample is then analyzed.

A fourth method of sample pre-concentration is precipitation. Centrifugally-cleared saliva is mixed with 1 volume of an ammonium sulfate solution at 50% saturation. After a 10 min incubation period at room temperature, the sample is centrifuged at 15,000×g for 30 min at room temperature. The supernatant is discarded. After another cycle of ammonium sulfate+centrifugation step and discarding of the second supernatant, the final pellet is resuspended and subjected to analysis.

A fifth method of preconcentration is anion-exchange, metal chelate-affinity or hydrophobic interaction or reverse-phase adsorption, optionally using an internal-surface reverse phase or another access-controlled adsorbent. For anion-exchange adsorption of sugars, operation at high pH (>9) is preferred.

All compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the disclosure as defined by the appended claims.

VII. REFERENCES

The following references, to the extent that they provide exemplary procedural or other details supplementary to those set forth herein, are specifically incorporated herein by reference.

International Publication No. WO2008072702A1
U.S. Pat. No. 8,465,940
K Daughters, ASR Manstead, K Hubble, A Rees, A Thapar, SHM van Goozen. Salivary oxytocin concentrations in males following intracanal administration of oxytocin: A double-blind, cross-over study. PLOS ONE (2015)
R. J. Linhardt, H. G. Bazin, Separation and Purification of Carbohydrates, in: Glycosci. Chem. Chem. Biol., 2002: pp. 63-74
R. A. Young, The Precipitation of Carbohydrates by Neutral Salts, J. Physiol. 22 (1898) 401-422.

The invention claimed is:

1. A method for analyzing a sample, the method comprising:
    (a) obtaining the sample comprising 1,5-anhydroglucitol and optionally a first species;
    (c) adding a first reagent to the sample, wherein the first reagent causes a first chemiluminescent or bioluminescent reaction with 1,5-anhydroglucitol in the sample; and
    (d) measuring a first light response resulting from the first chemiluminescent or bioluminescent reaction;
    (e) adding a second reagent to the sample, wherein:
        (i) the second reagent is added before or after the first reagent to the sample; and
        (ii) the second reagent causes a second chemiluminescent reaction with the first species in the sample;
    (f) measuring a second light response resulting from the second chemiluminescent reaction; and
    (g) comparing the first light response to the second light response to determine a ratio of 1,5-anhydroglucitol and the first species.

2. The method of claim 1, further comprising:
    (h) adding one or more additional reagents to cause the generation of light from 1,5-anhydroglucitol;
    (i) observing the amount of light produced from the sample of [h]; and
    (j) estimating the 1,5-anhydroglucitol from the light produced from the sample of [h].

3. The method according to claim 1, wherein the method further comprises adding a third reagent.

4. The method of claim 1, wherein the sample comprises saliva.

5. The method of claim 1, wherein the sample comprises urine, blood or interstitial fluid.

6. The method of claim 1, wherein the method further comprises separating the sample into two or more aliquots.

7. The method according to claim 1, wherein the first species is present and is selected from the group consisting of glucose, L-sorbose, D-xylose, D-galactose, glucono-δ-lactone, urea, creatinine, and creatine.

8. The method according to claim 1, wherein the second reagent is selected from the group consisting of glucose oxidase, galactose oxidase, glucokinase, galactokinase, urease, sarcosine oxidase, AHG-6-phosphate dehydrogenase and creatinase.

9. The method of claim 1, wherein the first reagent is selected from the group consisting of sorbose dehydrogenase, 1,5-anhydroglucitol phosphate-specific dehydrogenase, hexokinase, 1,5-anhydroglucitol specific oxidase and 1,5-anhydroglucitol specific dehydrogenase.

10. The method according to claim 9, wherein the method comprises adding an oxidant-removing or reductant-removing agent to the sample.

11. The method according to claim 1, wherein the first light response results from the reaction of a peroxidase, luminol, luciferase, a dioxetane, peroxyoxalate, or an acridine ester.

12. The method of claim 1, wherein measuring the first light response comprises measuring photons with a light detector selected from the group consisting of a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode, camera, cellular phone camera, web camera, and smart watch camera.

13. The method of claim 1, wherein one or more of the reagents are added to the sample via a microfluidic device.

14. The method of claim 1, wherein comparing the first light response to the second light response to determine a ratio of 1,5-anhydroglucitol and the second analyte comprises transmitting data to a computer processor.

15. The method of claim 1, further comprising accessing a lookup table or performing a calculation with the computer processor, wherein the table lookup or calculation provides an indication of a physiological condition.

16. The method of claim 1, further comprising normalizing the ratio based on a measurement of a marker in the sample.

17. The method of claim 1 which further comprises measuring blood glucose or hemoglobin A1c.

* * * * *